United States Patent
Avaltroni

[11] Patent Number: 5,989,197
[45] Date of Patent: Nov. 23, 1999

[54] AUTOMATIC BIOPSY NEEDLE DEVICE

[75] Inventor: Paolo Avaltroni, Mantova, Italy

[73] Assignee: Gallini S.R.L., Mirandola, Italy

[21] Appl. No.: 09/142,310

[22] PCT Filed: Mar. 7, 1997

[86] PCT No.: PCT/IB97/00209

§ 371 Date: Sep. 3, 1998

§ 102(e) Date: Sep. 3, 1998

[87] PCT Pub. No.: WO97/32524

PCT Pub. Date: Sep. 12, 1997

[30] Foreign Application Priority Data

Mar. 7, 1996 [IT] Italy .................................. BO96A0119

[51] Int. Cl.⁶ .................................................. A61B 10/00
[52] U.S. Cl. ............................ 600/567; 600/564; 606/167
[58] Field of Search ..................................... 600/562, 564,
600/567, 568; 604/21, 22, 164, 264; 606/167,
170, 171, 172, 181

[56] References Cited

U.S. PATENT DOCUMENTS

| | | | |
|---|---|---|---|
| Re. 34,056 | 9/1992 | Lindgren ................................. | 600/567 |
| 4,924,878 | 5/1990 | Nottka ..................................... | 600/567 |
| 4,944,308 | 7/1990 | Akerfeldt ................................ | 600/567 |
| 4,953,558 | 9/1990 | Akerfeldt ................................ | 600/567 |
| 5,172,702 | 12/1992 | Leigh et al. ............................. | 600/567 |
| 5,188,118 | 2/1993 | Terwilliger ............................. | 600/567 |
| 5,195,533 | 3/1993 | Chin et al. .............................. | 600/567 |
| 5,224,470 | 7/1993 | Schnepp-Pesch et al. ............. | 600/567 |
| 5,368,045 | 11/1994 | Clement et al. ........................ | 600/567 |
| 5,476,101 | 12/1995 | Schramm et al. ...................... | 600/567 |
| 5,535,755 | 7/1996 | Heske ...................................... | 600/567 |
| 5,551,442 | 9/1996 | Kanner et al. .......................... | 600/567 |
| 5,564,436 | 10/1996 | Hakky et al. ........................... | 600/567 |

FOREIGN PATENT DOCUMENTS 0 238 461 A1  2/1986  European Pat. Off. .

*Primary Examiner*—Cary O'Connor
*Assistant Examiner*—Charles Marmor, II
*Attorney, Agent, or Firm*—Nims, Howes, Collison, Hansen & Lackert

[57] ABSTRACT

A biopsy needle device includes a stem slidably inserted into a cannula. Both the stem and the cannula are slidably supported by a box-shaped case. The box-shaped case houses a first movable assembly; a second movable assembly; a charging mechanism associated to the first and the second movable assemblies; an unlocking element; and an enabling element. The first movable assembly supports the cannula and is subject to a first spring. The second movable assembly supports the stem and is subject to a second spring. The charging mechanism is operable from outside the case in order to charge the first spring and the second spring at a charging phase, wherein the movable assemblies are engaged with the case by hooking mechanisms. The unlocking element releases the hooking mechanisms at an intermediate phase, wherein the second spring is discharged, and at a discharging phase, wherein the first and the second springs are both discharged. The enabling element is rotatably supported by the case for enabling axial movement of the unlocking element when the device switches in sequence between the charging phase, the intermediate phase, and the discharging phase.

11 Claims, 3 Drawing Sheets

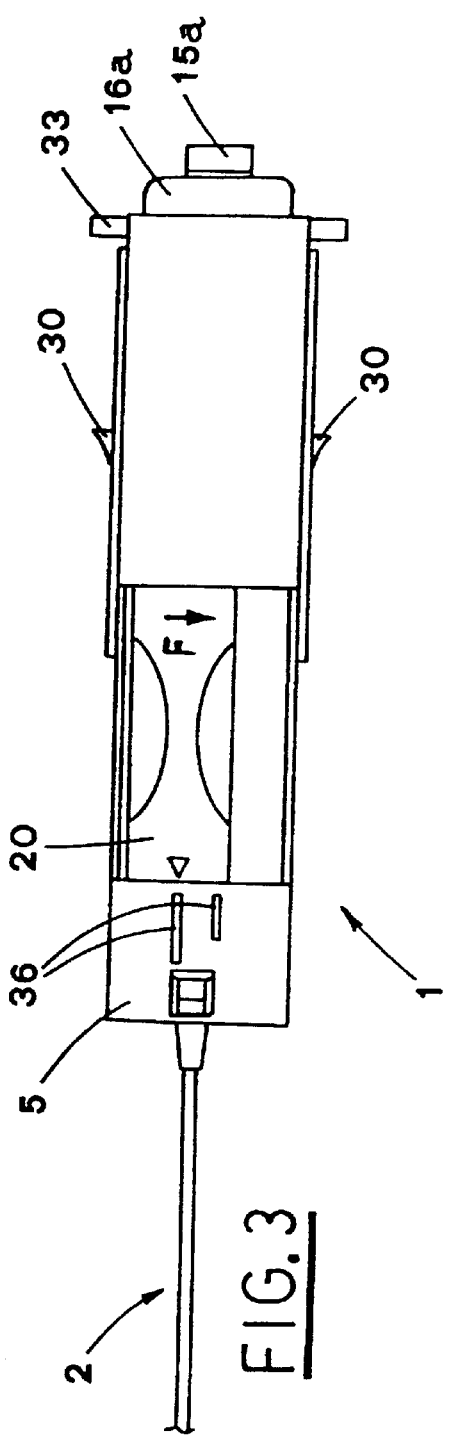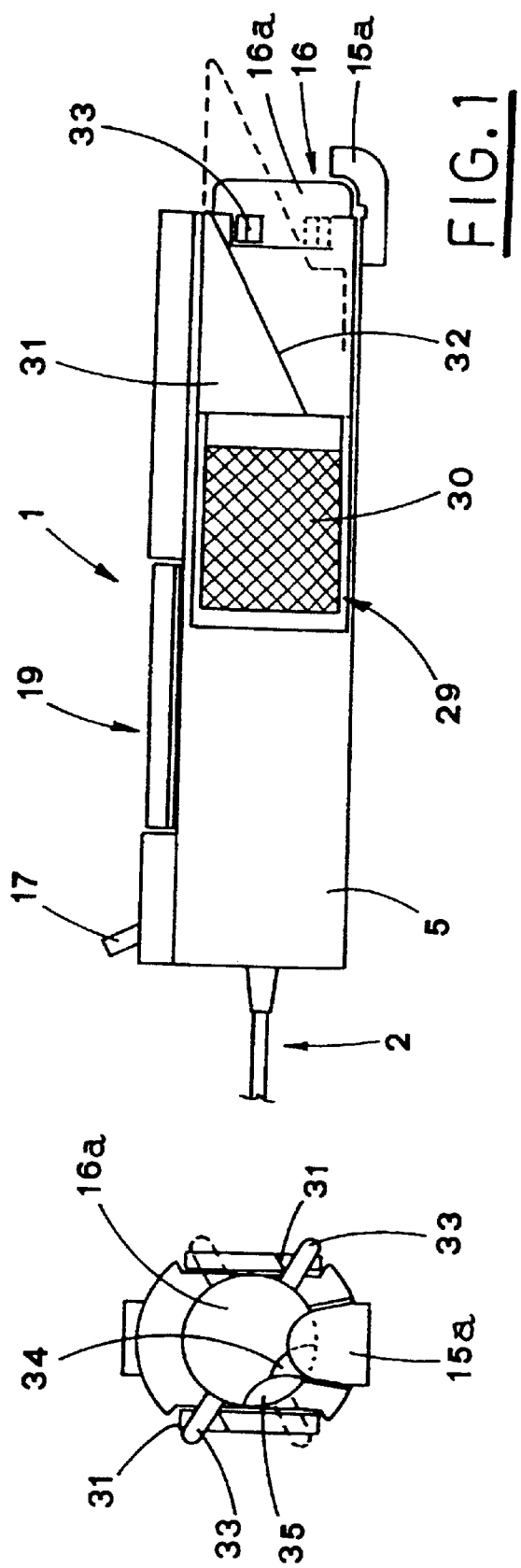

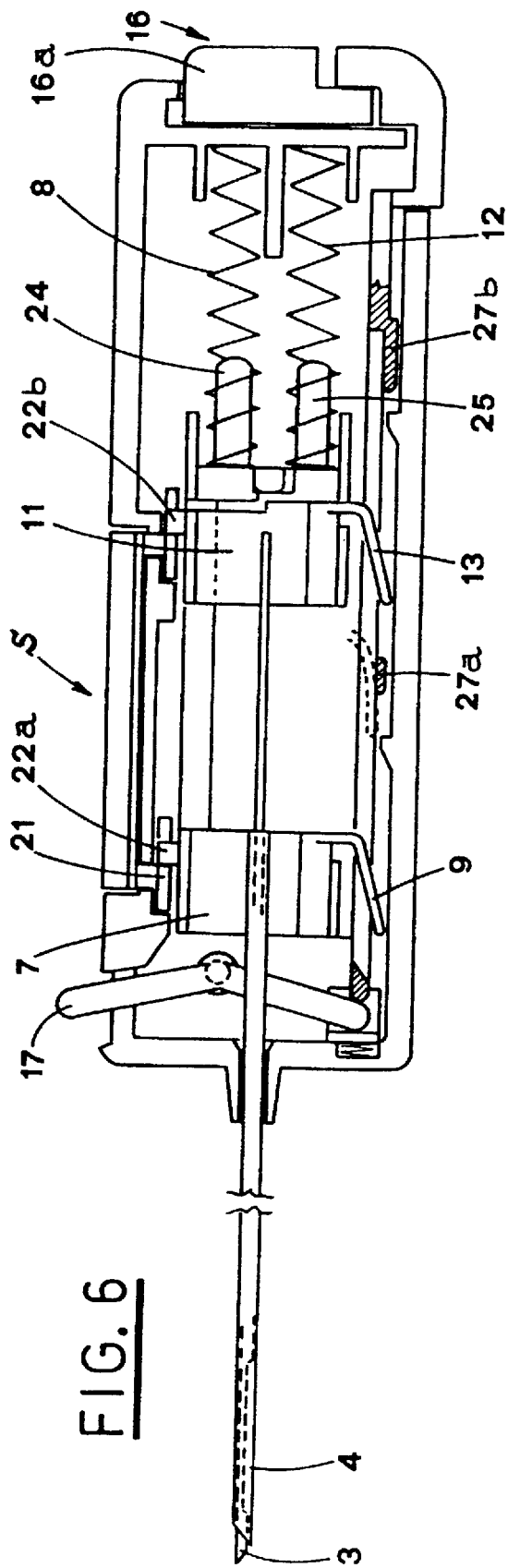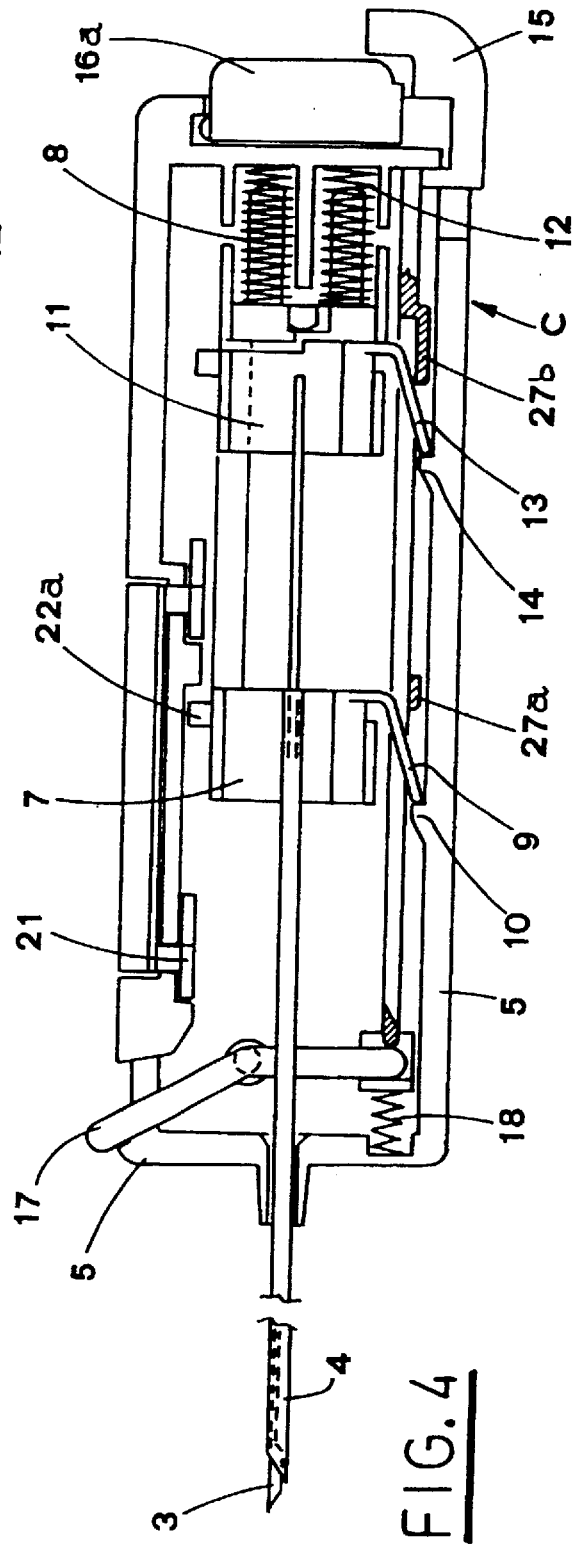

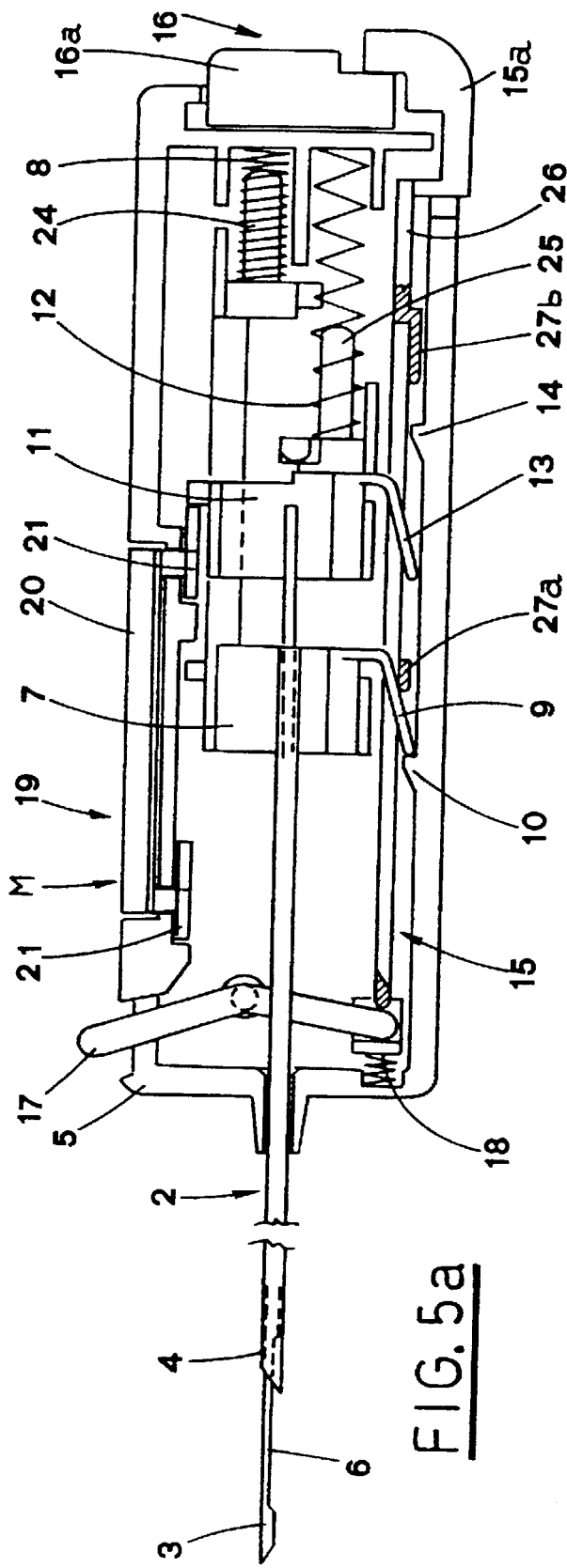
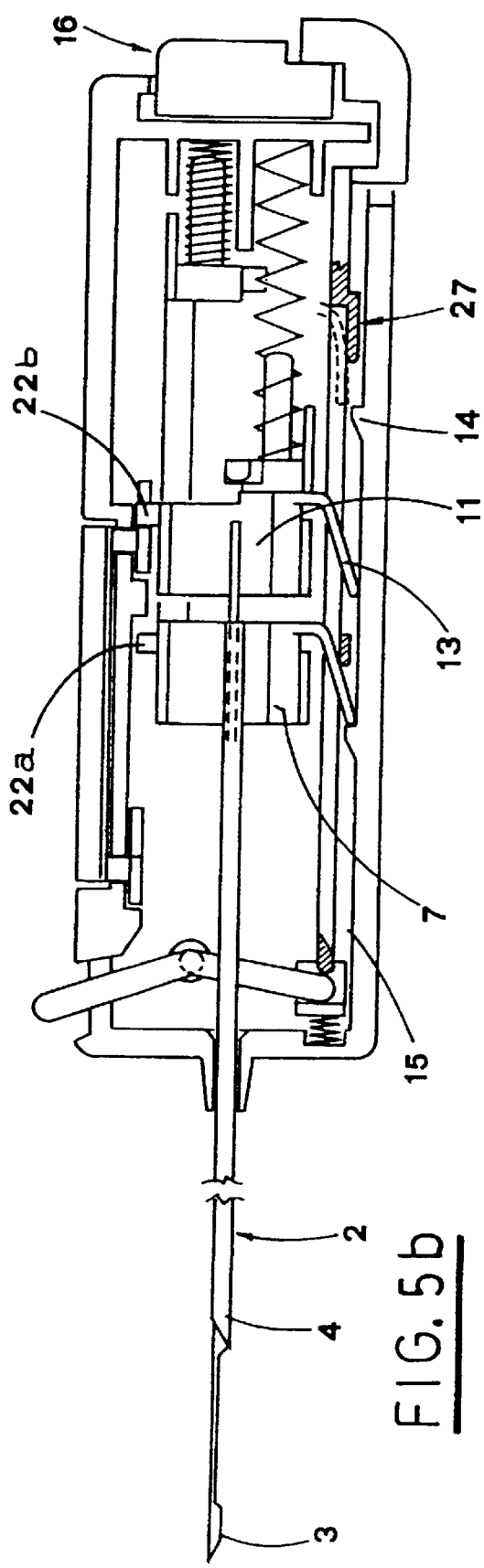

AUTOMATIC BIOPSY NEEDLE DEVICE

TECHNICAL FIELD

The present invention relates to the technical sector concerning surgical instruments fit to be used for taking samples of tissues, cells or liquids from a living organism, in order to make a diagnosis.

More particularly, the present invention refers to a needle device, preferably a disposable needle device, for automatically or semi-automatically carrying out a biopsy, in order to take a sample of the organ to be analysed.

BACKGROUND ART

The known biopsy needle devices, to which will be shortly referred to as biopsy needles in the following description, comprise a needle consisting of a cannula, holding a slidable stem inside it. The distal end of said stem projects from the cannula distal end, and can arrange a portion of an organ to be sampled, after it has been cut from a guillotine-like point, located at the cannula distal end, because of the mutual approach of said distal ends The biopsy needles are then based on the principle of cutting a pre-defined organ portion by inserting them into the organ to be analysed, then arranging the cut tissue portion in the cavity which is comprised between the stem and the cannula, when this latter slides on the same stem.

The currently known biopsy needles are manually activated. Their cannula is locked to the needle support, while the stem proximal end is slidably supported by a movable assembly, fit to move the stem distal end with respect to the same end of the cannula.

The movable assembly stroke is adjustable in order to cut a pre-defined amount (in length) of the tissue sample to be taken.

Said manually activated needles are reasonably simple devices, but they lack in accuracy during the needle positioning and tissue sampling phases: in fact, it is difficult for an operator to coordinate by hand the mutual sliding of the needle stem and cannula, when both are independently movable and when the same operator must hold both with his hands.

Some biopsy needles which are automatically or semi-automatically operated are also known. They are manually pre-charged, and then inserted near the sampling area. They are then able to automatically carry out a first operating phase, wherein the distal stem cavity is ejected out of the cannula, and then a second operating phase, wherein a portion of tissue occupying the said cavity is cut by means of a guillotine-like effect when the cannula slides on the stem, until the cavity is totally enclosed into the cannula. The aforesaid needles can also work in a semi-automatic way, by executing the above described second operating phase not automatically, but by activating a manual control. This latter normally unlocks a locking member, which prevents said second phase from being activated.

In said biopsy needles the stem and cannula are supported each one by a respective assembly. Moreover, they are subject to elastic reaction forces, which are normally supplied by suitably arranged springs, in order to "charge" the needle, and then to be able to automatically or semi-automatically "shoot" with the same needle.

In the "charge" phase the stem cavity is placed inside the cannula, and the distal ends of said stem and cannula are held as close as possible to the needle body. This normally consists of a box-shaped case, which slidably supports the whole needle. It also contains the movable assemblies, the charge springs and further accessory members, e.g. safety devices fit to prevent any accidental needle "shooting". During said charging, phase the above safety devices are automatically connected, and some suitable springs are pre-charged in order to enable the needle for shooting.

During the shooting phase, after the security device has been disconnected and the needle has been put close to the organ to be analysed, it is possible, by operating the shooting "trigger", to eject the stem and then the cannula. This takes place because the springs acting on their respective movable assemblies are sequentially discharged. As described above, the shooting phase can take place in a semi-automatic way, by ejecting only the stem first, and then ejecting the cannula, after its locking device has been disconnected A known kind of biopsy needle is charged by lifting from the needle body an element hinged thereon. Said element is connected to a mechanism operating on the springs to be charged, which is able to automatically insert the safety device, once the needle reaches its wide apart position, with respect to the same needle body.

In a further kind of known biopsy needle, the shooting springs are charged by mutually rotating two box-shaped cases, by means of a spring charging mechanism, which is operated by a plurality of helical guides. This kind of needle also comprises a shooting safety device, which is inserted once the charge operations have been completed.

A further known biopsy needle is charged by means of a cursor, which operates on the charging springs, arranged at the end of the biopsy needle body close to the outer needle portion. It is also axially slidable on that body. An operator charges the springs by pressing on the cursor head. This furthermore allows the safety device to be inserted.

The known biopsy needles have some common features, as the shooting "trigger", button or lever, which is placed near the free end of the needle body. They are also provided with means for adjusting the stem penetration depth and for defining the length of the tissue sample to be taken. A further common feature is that stem and cannula are charged simultaneously.

The main drawback of the above described biopsy needles is that their trigger can be placed only at the free end of the biopsy needle body, that is at a somewhat awkward position for an operator which wants to activate the needle during the shooting phase. In fact, the sample to be taken is at the opposite end with respect to said trigger, and operating this latter causes an axial force to be applied to the needle. This can displace the needle point from its correct position inside the sampled organ. In other words, the operator must hold the needle body with one hand, while operating the trigger with the other hand, in order to compensate the axial forces acting on the trigger and to prevent the needle point from being displaced. Thus, the operator cannot simultaneously use any other instrument (e.g. an ultrasound scanner probe), and the whole sampling operation decreases in accuracy. This lack of accuracy is especially evident when a small tissue area inside an organ must be sampled.

A further drawback is that the needle charge mechanisms are often very complex and of difficult operation, because operators have to study how the charging system works, and to acquire a good skill about its working.

DISCLOSURE OF THE INVENTION

The main object of the present invention is therefore to propose a completely automatic needle device for carrying out biopsy samplings, also provided with a shooting system fit to be operated with only one operator's hand, without any needle point movement, thus not compromising the sampling accuracy.

A further object of the present invention is to allow the cannula to be independently charged with respect to the stem, in order to guarantee the operator as many degrees of freedom as possible in carrying out the biopsy. This also makes the charging operation much more easy, since the charging force during a single element charging is obviously smaller than that required for simultaneously charging both cannula and stem.

A further object of the invention is to provide a needle device which is of easy and comfortable operation.

A further object of the present invention is to provide a needle device of easy manufacturing and safe and accurate in use.

The above mentioned objects are carried out, according to the contents of the independent claim, by a biopsy needle device, consisting of a stem slidably inserted into a cannula, both of them being slidably supported by a box-shaped case, said stem being provided with a cavity near its distal end, and fit to hold a sample of an organ to be examined, into which the said needle is inserted, after the sample has been cut by said cannula.

Said device moreover comprises:

a first movable assembly, having the proximal end of said cannula fixed thereto, a first elastic element being also in contact with said first movable assembly, this latter being moreover provided with first hooking means, fit to engage corresponding first stops made on the said case walls;

a second movable assembly, having the proximal end of said stem fixed thereto, a second elastic element being in contact with said second movable assembly, this latter being moreover provided with second hooking means, fit to engage corresponding second stops made on said case walls;

charging means of said first movable assembly and second movable assembly, which are operable from outside said case;

an unlocking element of said first hooking means and second hooking means from their corresponding stops;

enabling means, rotatably supported by said case, interposed between this latter and said unlocking element, fit to enable the said unlocking element axial moving.

BRIEF DESCRIPTION OF THE DRAWINGS

The features of the present invention are underlined in the following, with referance to attached drawing tables, in which:

FIG. 1 is a partial side view of the biopsy needle device of the present invention;

FIG. 2 is a front view of the free head of the needle body of FIG. 1;

FIG. 3 is a top view of the needle of FIG. 1;

FIG. 4 is a sectional, enlarged partial view of the needle body of FIG. 1, at a charging phase;

FIGS. 5a and 5b are sectional, enlarged partial views of the needle of FIG. 1, at intermediate operating phases, respectively showing a first and a second stem penetration depth into the organ to be analysed;

FIG. 6 is a sectional, enlarged partial view of the needle body of FIG. 1, at a charging phase.

BEST MODE OF CARRYING OUT THE INVENTION

With reference to FIGS. 1 to 6, numeral 1 indicates a biopsy device provided with a needle 2. The needle 2 comprises a stem 3 slidably inserted into a cannula 4, said stem 3 and cannula 4 being slidably supported by a box-shaped case 5, from which they project for almost all their length.

The stem 3 is provided with a cavity 6, near its distal end, and fit to arrange a sample of the organ to be examined during the biopsy operation.

The device 1 moreover comprises a first movable assembly 7, a second movable assembly 11, charging means 29, an unlocking element 15 and enabling means 16.

The first movable assembly 7 carries the cannula 4 proximal end on one side; between the other side of said first movable assembly 7 and the bottom inner wall of the case 5 there is inserted a first elastic element 8, which preferably consists of a spring, partially wound on a first support 24, projecting from the fist movable assembly 7 and turned towards the case 5 bottom. Said first movable assembly 7 is provided with first hooking means 9, essentially consisting of a flexible wing, fit to engage corresponding first stops 10 made on the inner walls of the case 5.

As for the first assembly 7, the second movable assembly 11 carries on one side the proximal end of the stem 3, while a second elastic element 12 is between the other side of the movable assembly 11 and the inner wall of the case 5, preferably consisting of a spring, guided by a second support 25 projecting from the movable assembly 11 body. This latter is provided with hooking means 13, fit to engage corresponding second stops 14 made on the inner walls of the case 5.

The charging means 29 essentially consist of a pair of sliding blocks 30, each of them being arranged sideways on the case, and being also provided with a projection 31, turned towards the case 5 bottom and having an inclined plane 32 turned towards the inside of the case.

The charging means are supported by the case 5 so that the two inclined planes have opposite slopes.

It is to be noted that the first movable assembly 7 and the second movable assembly 11 can slide axially inside the case 5; they are also independently movable, since the sliding blocks 30, to which they are respectively fixed, are independently movable.

The unlocking element 15 of the first hooking means 9 and second hooking means 13, for unlocking them from the corresponding first stop 10 and second stop 14, consists of a central bar 26, to the outer end of which a push button 15a is fixed. This latter projects from the case 5 at its free end. Bar 26 is provided with holes, into which the first hooking means 9 and second hooking means 13 are free to slide, and with prominences 27, respectively front 27a and rear 27b, which are transversely fixed to said holes, being also able to unengage the hooking means 9,13 from their corresponding first stops 10 and second stops 14.

The first arm of a lever 17 engages the inside end of bar 26. The second arm of lever 17 extends out from the case 5, while the lever 17 is pivoted to the case 5 at the joint between the first arm and the second arm.

A spring 18 is placed between the free end of the unlocking element 15 and the inner wall of the case 5, which helps a correct positioning of said element 15 during the device 1 operating sequence, as described in the following.

The enabling means 16 consist of a central, circular body 16a, which is rotatably supported at the outer bottom of the case 5, from which case two projections 33 extend in a radial direction, at opposite diametral ends, each projection 33 being fit to slide on the corresponding inclined plane 32 of each sliding block 30. The central body 16a includes a pair of recesses, an outer recess 34 and one inner recess 35, said outer recess 34 being shallower than said inner recess 35, with respect to the outer body surface.

The device 1 moreover comprises depth adjusting means 19, fit to adjust the sampling depth. This latter consists of a cursor 20, which is external with respect to the case 5, and is supported by this latter in a transversely sliding engagement. Two stops 21 are fixed to said cursor 20, inside the case 5. Each stop 21 consists of a pair of projections, which are selectable by transversely moving said cursor 20, so that they match corresponding projections 22a, 22b, respectively projecting from the first movable assembly 7 and from the second movable assembly 11, thus defining two depth levels for the needle 2, corresponding to a complete exposition for the cavity 6, or to its partial covering by the cannula 4. Said depths preferably correspond to 15 millimetres and 22 millimetres.

Operating said needle device is extremely simple, because an operator, before inserting the needle in the organ to be sampled, "charges" the needle 2 by activating a charging phase C of the device 1, which is shown in FIG. 4. The operator moves the sliding blocks 30, synchronously or each one separately, by sliding them on the outer flanks of the case 5, towards its bottom, so that the springs 8 and 12 are pressed between the case 5 and, respectively, the first movable assembly 7 and second movable assembly 11, until the first hooking means 9 engages the corresponding first stop 10 and the second hooking means 13 engages the second stop 14. It is to be noted that said first and second hooking means 9 and 13 consist of flexible wings, preferably made of a plastic material, which tend to divaricate, thus easily engaging their corresponding case fixed stops 10, 14, and locking the first movable assembly 7 and the second movable assembly 11, in a withdrawn position. In this position they are subject to the elastic forces generated by the respective springs 8 and 12.

The needle 2 so charged in the device charging phase C holds a condition of stable equilibrium, since the enabling means 16 prevents the push button 15a or to the lever 17 from releasing the first movable assembly 7 and the second movable assembly 11, and then from "shooting" the needle 2. This is achieved because the free end of the push button 15a contacts the outer surface of the central body 16a of the enabling means 16 since, while the sliding blocks 30 are moving, the inclined planes 32 allow the central body 16a to rotate, until its outer surface is turned towards the free end of the push button 15a, substantially with no slack.

It is to be noted that the sliding blocks 30 are separately operable, thus the operator is able to charge the needle 2 by using a small force, on condition that it is enough, by example, to exceed the elastic force of a single spring 8,12. To achieve this, the operator moves the sliding blocks 30 separately.

Once the needle has been charged, the stem cavity 6 is completely enclosed by the cannula 4, and the stem 3 and cannula 4 distal ends are placed close to the case 5. Moreover, for any particular reason, the operator is allowed to charge only the cannula 4, so that the cavity 6 is at least partially uncovered at the end of the charging phase C.

At this point the operator is just required to select the sampling depth by moving the cursor 20 (according to arrow F of FIG. 3), by example at one of two pre-defined depth markers 36, as shown in FIG. 3. The operator inserts then the needle 2 into the organ to be examined according to known techniques, normally until the needle 2 point reaches the right site in the tissue being sampled.

The operator can then decide to set the device 1 for completely automatic operating mode, or for semi-automatic operating mode, simply by suitably operating the enabling means 16.

If the automatic operating mode has been selected, the operator rotates the central body 16a so that the push button free end 15a faces the inner recess 35, deeper than the outer recess 34 with respect to the free surface of body 16a. Then, the operator simply presses the push button 15a or, alternately, he pulls the lever 17, in order to start up in sequence an intermediate phase M and a charging phase S.

With particular reference to FIGS. 5a and 5b, the intermediate phase M comprises the stem 3 to be ejected from the cannula 4. The stem 3 pierces the tissue to be sampled, because of the thrust provided to the movable assembly 11 by the spring 12. This latter is released to an extended position because the rear prominence 27b of bar 26 lift the second hooking means 13, disengaging them from the second stops 14.

The stem 3 stroke is limited by a prominence of the corresponding cursor stop 21, which contacts the prominence 22b of the second movable assembly 11. The stop 21 prominence matches the sampling depth, which was pre-set by transversely moving the cursor 20. More particularly, FIG. 5a shows the stem 3 depth when the cursor 20 is set at the shorter depth marker 36 shown in FIG. 3. In a similar way, FIG. 5b shows the operating phase M, wherein a stem 3 bigger depth has been selected, corresponding to a cursor 20

With particular reference to FIG. 6, it can be seen that the bar 26 continues its moving, by consequence of a pressure applied by the operator to the push button 15a or to the lever 17, thus causing the bar front prominence 27a to disengage the first hooking means 9 from the first stops 10. Therefore, the spring 8 is released and pushes the first movable assembly 7 forwardly until its prominence 22a goes in contact with the corresponding prominence of cursor stop 21. Said condition defines a discharging phase S for the device 1, wherein the cavity 6 is completely enclosed by the cannula 4, and the cut sample is enclosed between said cannula and the cavity bottom.

The only operation which the operator has to perform is now to extract the needle 2 from the organ from which the sample has been taken.

The semi-automatic device operating mode is substantially identical to the above described automatic operating mode. The only difference consists in that the operator, once the needle 2 has been inserted into the organ to be examined, rotates the central body 16a so that the outer recess 34, which is less deep than the inner recess 35, faces the push button 15a free end. Afterwards the operator presses the push button 15a or, if he prefers, pulls the lever 17 in order to start the intermediate phase M, i.e. to "shoot" the stem 3 according to the above described operating mode. Then he rotates the central body 16a again, until the inner recess 35 faces the push button 15a free end, and operates this latter or the lever 17 again. This allows the device 1 to switch from the intermediate phase M to the discharge phase S, according to the above described operating mode.

It is useful to highlight that the device double "shooting" system is very important. In fact, said device 1 can be used both by means of a rear push button 15a and by means of a front lever 17. This gives the operator a great advantage, because he can easily grip the device, and better operate this latter. The operation of carrying out the biopsy and matching the right area to be sampled become much more accurate.

The main advantage of the present invention is that a biopsy needle device, automatically or semi-automatically operated, is provided, which is moreover provided with an easily and effectively operating shooting system. Operations can be carried out by an operator simply by using only one hand, without causing any involuntary needle displacement from the area to be sampled, and any casual movement of the needle point.

A further advantage is to provide a device able to allow the cannula can be charged both simultaneously to or independently from the stem, in order to guarantee the operator all the possible degrees of freedom in carrying out the biopsy. Moreover, this makes much more easy the biopsy needle charging operation, because the operator can use, if he prefers, a reduced charging force by independently charging the cannula and stem.

A further advantage of the present invention is to provide a biopsy automatic device of simple manufacturing and fit to be easily and safely used by the medical staff.

I claim:

1. A biopsy needle device comprising a needle (2) having a stem (3) slidably inserted into a cannula (4); the stem (3) and the cannula (4) being slidably supported by a box-shaped case (5); said stem (3) being provided with a cavity (6) near a distal end thereof, said stem being fit to hold a sample of an organ to be examined, into which said needle (2) is inserted, after the sample has been cut by said cannula (4), said device (1) further comprising:

a first movable assembly (7), having a proximal end of said cannula (4) fixed thereto, a first elastic element (8) being in contact with said first movable assembly (7), said first movable assembly (7) having first hooking means (9) for engaging a corresponding first stop (10) made on walls of the case (5), at a charging phase (C) of said device (1), wherein said first elastic element (8) is stressed so that it generates an elastic reaction force on said first movable assembly (7);

a second movable assembly (11), having a proximal end of said stem (3) fixed thereto, a second elastic element (12) being in contact with said second movable assembly (11), said second movable assembly (11) having second hooking means (13) for engaging a corresponding second stop (14) made on walls of the case (5), at a charging phase (C) of said device (1) wherein said second elastic element (12) is stressed so that it generates an elastic reaction force on said second movable assembly (11);

charging means (29) for charging said first movable assembly (7) and second movable assembly (11), said charging means (29) being operable from outside said case (5), wherein moving the charging means (29) between two extreme positions causes the respective first (7) and second (11) movable assemblies to be dragged, so that said device (1) switches from a discharging phase (S) to said charging phase (C), said first elastic element (8) and said second elastic element (12) being discharged during said discharging phase (S); an unlocking element (15) for releasing said first hooking means (9) and second hooking means (13) from the corresponding stops (10,14), respectively at said discharging phase (S) and at an intermediate phase (M) of said device (1) wherein said cavity (6) is not covered by said cannula (4) and said second elastic element (12) is discharged while said first elastic element (8) is charged;

and enabling means (16), rotatably supported by said case (5), interposed between said case (5) and said unlocking element (15), for enabling axial movement of said unlocking element (15), in order to allow said device (1) to switch from said charging phase (C) to said intermediate phase (M) and then to said discharging phase (S), said enabling means being automatically operated by said charging means (29) at said charging phase (C).

2. A device according to claim 1, further comprising depth adjusting means (19) for taking said sample from the organ to be examined, said depth adjusting means (19) consisting of a cursor (20), placed outside of the case (5) and transversely movable to pre-defined positions, thus defining an engagement between a pair of stops (21) fixed to said cursor (20) and corresponding prominences (22a,22b), respectively provided on the first movable assembly (7) and on the second movable assembly (11), for setting an axial stroke thereof.

3. A device according to claim 2, wherein said stops (21) of said depth adjusting means (19) are symmetrically provided with a pair of offset projections, which are selectable by transversely moving said cursor(20) to match the selected projections with said prominences (22a,22b) to define two sampling depth levels, respectively corresponding to conditions of a complete cavity (6) uncovering or of a partial cavity (6) covering by the cannula (4).

4. A device according to claim 1, wherein said unlocking element (15) consists of a central bar (26) having a push button (15a) fixed to an inner end thereof, said push button (15a) being arranged outside of said case (5), said bar (26) being provided with prominences (27) at a free end thereof fit to disengage said first hooking means (9) and second hooking means (19) from the corresponding first stop (10) and second stop (14), at said intermediate phase (M) and discharging phase (S).

5. A device according to claim 4, wherein a first arm of a lever (17) engages the free end of said bar (26), a second arm of said lever (17) projecting outside of said case (5), and moving of the second arm of said lever (17) allows said unlocking element (15) to move axially at said intermediate phase (M) and discharging phase (S).

6. A device according to claim 4, wherein said enabling means (16) consists of a circular central body (16a), from which two projections (33) project radially and at opposed diametral ends, a pair of recesses being made on an outer surface of said central body (16a), respectively an outer recess (34) and an inner recess (35), fit to be matched by said push button (15a), respectively at said intermediate operating phase (M) and discharging operating phase (S), when said push button (15a) contacts the outer surface of said central body (16a) at said charging phase (C).

7. A device according to claim 1, wherein a spring (18) is arranged between a free end of said unlocking element (15) and a inner wall of said case (5), said spring (18) defining the positioning of said unlocking element (15) at said charging phase (C) and discharging phase (S).

8. A device according to claim 1, wherein said first movable assembly (7) and second movable assembly (11) are respectively provided with a first support (24) for said first elastic element (8) and with a second support (25) for said second elastic element (12).

9. A device according to claim 8, wherein said first elastic element (8) and second elastic element (12) consist of a pair of springs.

10. A device according to claim 1, wherein said charging means (29) consists of a pair of sliding blocks (30), each of said blocks (30) being provided with a projection (31) having an inclined plane (32), on that a corresponding projection (33) of said enabling means (16) slides, when each of said sliding blocks (30) is moved at said charging phase (C).

11. A device according to claim 10, wherein said sliding block (30), which is associated to said first movable assembly (7), is movable independently from the corresponding sliding block (30) which is associated to said second movable assembly (11).

* * * * *